US008226894B2

United States Patent
Miyake et al.

(10) Patent No.: US 8,226,894 B2
(45) Date of Patent: Jul. 24, 2012

(54) ULTRASONIC TREATMENT APPARATUS

(75) Inventors: Haru Miyake, Nagoya (JP); Takamura Miyake, Toyota (JP)

(73) Assignee: Haru Miyake (JP)

( * ) Notice: Subject to any disclaimer, the term of this patent is extended or adjusted under 35 U.S.C. 154(b) by 376 days.

(21) Appl. No.: 12/312,919

(22) PCT Filed: Dec. 19, 2007

(86) PCT No.: PCT/JP2007/074402
§ 371 (c)(1),
(2), (4) Date: Jun. 1, 2009

(87) PCT Pub. No.: WO2008/075708
PCT Pub. Date: Jun. 26, 2008

(65) Prior Publication Data
US 2009/0287142 A1 Nov. 19, 2009

(30) Foreign Application Priority Data
Dec. 20, 2006 (JP) .................. 2006-342984

(51) Int. Cl.
B06B 1/00 (2006.01)
C02F 1/68 (2006.01)
C02F 1/70 (2006.01)
C02F 1/72 (2006.01)
A61M 35/00 (2006.01)

(52) U.S. Cl. ........ 422/128; 210/749; 210/757; 210/758; 604/293

(58) Field of Classification Search .................. 422/128; 210/749, 757–758; 604/293
See application file for complete search history.

(56) References Cited

U.S. PATENT DOCUMENTS

2003/0164308 A1*  9/2003  Schlager et al. .............. 205/701
2008/0289971 A1*  11/2008  Shigihara et al. ............. 205/687

FOREIGN PATENT DOCUMENTS

| JP | 56-84840 | 8/1981 |
| JP | 2003-245663 | 9/2003 |
| JP | 2004-135954 | 5/2004 |
| KR | 2002-0066879 | 8/2002 |
| WO | WO 03/086479 | 10/2003 |
| WO | WO 2005/014489 | 2/2005 |
| WO | WO 2006/054552 | 5/2006 |
| WO | WO 2007/069439 | 6/2007 |

OTHER PUBLICATIONS

Machine translation of Application JP2006-544111 provided by JPO, retrieved Sep. 12, 2011.*

* cited by examiner

Primary Examiner — Walter D Griffin
Assistant Examiner — Christopher Vandeusen
(74) Attorney, Agent, or Firm — Bacon and Thomas, PLLC

(57) ABSTRACT

An ultrasonic treatment apparatus treats a part of the body without use of a medical agent. The ultrasonic treatment apparatus includes a treatment vessel, an ultrasonic element, an ultrasonic element driving circuit, and an operation section. The treatment vessel holds a medium and the ultrasonic element generates ultrasonic waves through the medium to decompose the water in the medium to thereby generate hydroxyl radicals. The ultrasonic element driving circuit drives the ultrasonic element. The operation section is used to set sterilization conditions determined by the amount of hydroxyl radicals generated by the ultrasonic waves.

7 Claims, 4 Drawing Sheets

ULTRASONIC TREATMENT APPARATUS

TECHNICAL FIELD

The present invention relates to an ultrasonic treatment apparatus.

BACKGROUND ART

Conventionally, there has been provided an ultrasonic sterilizing apparatus, which is an ultrasonic treatment apparatus for treating a diseased part of the body (e.g., for treatment of athlete's foot) by generating ultrasonic waves and radiating the waves onto the diseased part (i.e., a part to be treated) to which a medical agent has been applied, to thereby cause the agent to penetrate into the diseased part (see, for example, Patent Document 1).

Patent Document 1: Japanese Patent Application Laid-Open (Kokai) No. 2004-135954

DISCLOSURE OF THE INVENTION

Problems to be Solved by the Invention

However, when ultrasonic waves are radiated onto a diseased part without use of a medical agent, conventional ultrasonic sterilizing apparatuses have a drawback in that they cannot sufficiently sterilize *Trichophyton* and similar microorganisms which cause athlete's foot.

In view of the foregoing, an object of the present invention is to solve the above-mentioned problem of conventional ultrasonic sterilizing apparatuses, and to provide an ultrasonic treatment apparatus with which a part to be treated can be treated without use of a medical agent.

Means for Solving the Problems

In order to achieve the aforementioned object, the ultrasonic treatment apparatus of the present invention comprises a treatment vessel for accommodating a medium; an ultrasonic element for generating ultrasonic waves in the treatment vessel, irradiating the medium accommodated in the treatment vessel with the ultrasonic waves, and decomposing water present in the medium to generate hydroxyl radicals; an ultrasonic element driving circuit for driving the ultrasonic element; and an operation section for setting given sterilization conditions determined based on the amount of the generated hydroxyl radicals upon generation of the ultrasonic waves.

Effects of the Invention

According to the present invention, the ultrasonic treatment apparatus comprises a treatment vessel for accommodating a medium; an ultrasonic element for generating ultrasonic waves in the treatment vessel, irradiating the medium accommodated in the treatment vessel with the ultrasonic waves, and decomposing water present in the medium to generate hydroxyl radicals; an ultrasonic element driving circuit for driving the ultrasonic element; and an operation section for setting given sterilization conditions determined based on the amount of the generated hydroxyl radicals upon generation of the ultrasonic waves.

In this case, since the aforementioned structure enables setting of desired sterilization conditions determined by the amount of hydroxyl radicals generated by means of ultrasonic waves, greatly improved sterilization effect can be obtained.

DESCRIPTION OF REFERENCE NUMERALS

10: apparatus main body
11: treatment vessel
13: operation section
21: ultrasonic element driving circuit
87: ultrasonic element

BEST MODE FOR CARRYING OUT THE INVENTION

An embodiment of the present invention will next be described in detail with reference to the drawings. First, an ultrasonic sterilizing apparatus serving as an ultrasonic treatment apparatus will be described.

Figure 1:
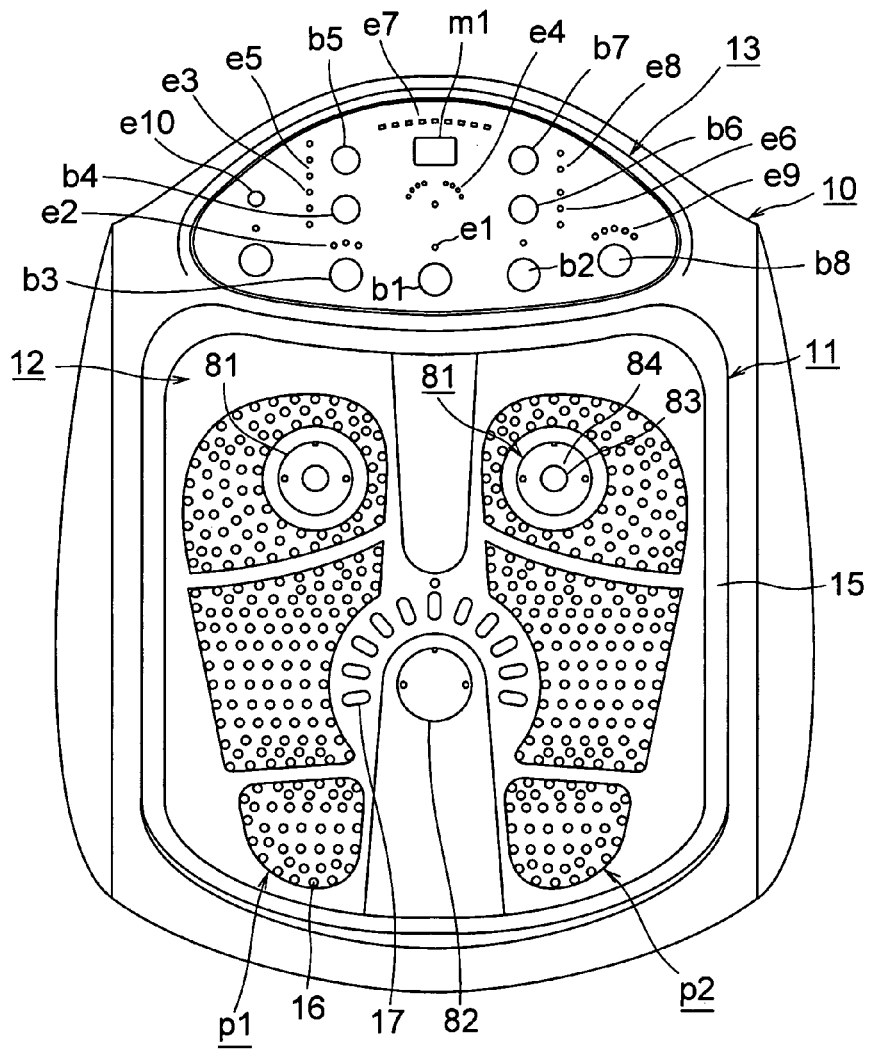
FIG. 1 Plan view of an ultrasonic sterilizing apparatus according to an embodiment of the present invention.
Figure 2:
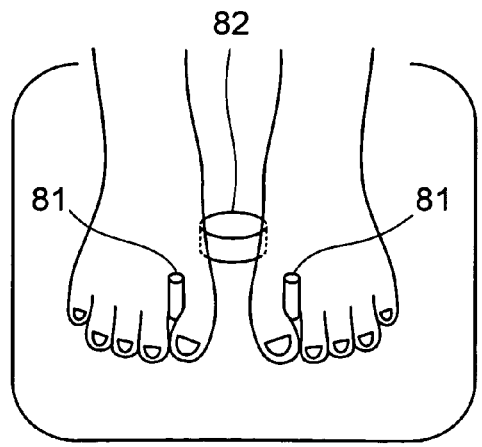
FIG. 2 Diagram showing how the feet are placed in the ultrasonic sterilizing apparatus according to the embodiment of the present invention.
Figure 3:
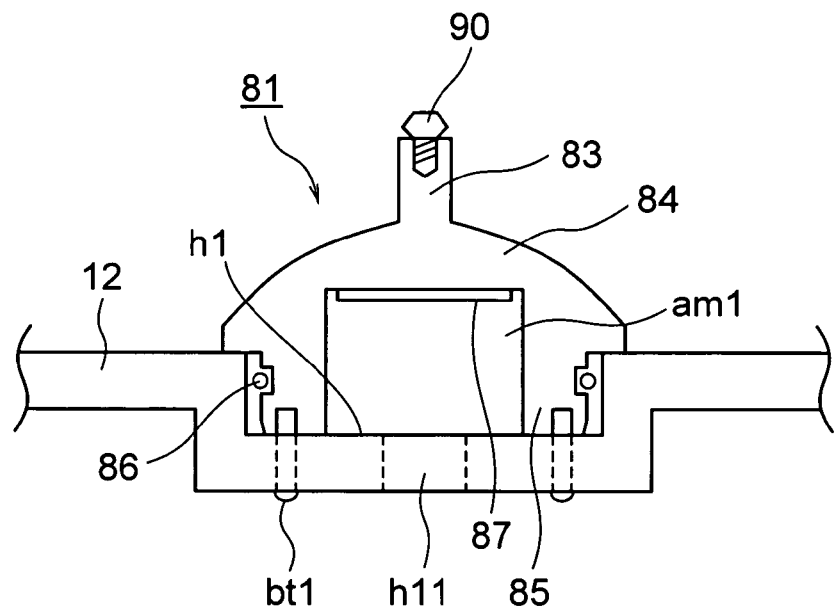
FIG. 3 Diagram showing how a pin-shaped ultrasonic vibrator is attached to the ultrasonic sterilizing apparatus according to the embodiment of the present invention.
Figure 4:
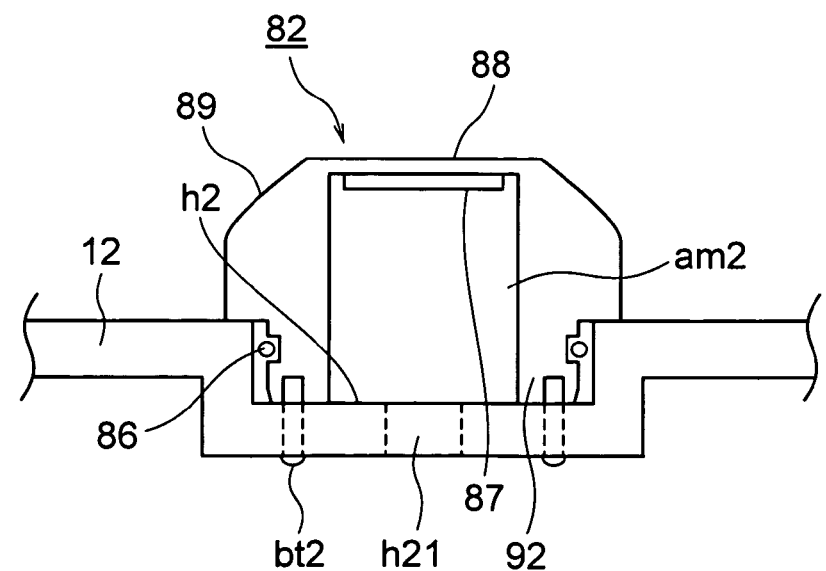
FIG. 4 Diagram showing how a flat-shaped ultrasonic vibrator is attached to the ultrasonic sterilizing apparatus according to the embodiment of the present invention.

FIG. 1 is a plan view of an ultrasonic sterilizing apparatus according to an embodiment of the present invention. FIG. 2 is a diagram showing how the feet are placed in the ultrasonic sterilizing apparatus according to the embodiment of the present invention. FIG. 3 shows how a pin-shaped ultrasonic vibrator is attached to the ultrasonic sterilizing apparatus according to the embodiment of the present invention. FIG. 4 shows how a flat-shaped ultrasonic vibrator is attached to the ultrasonic sterilizing apparatus according to the embodiment of the present invention.

In FIG. 1, reference numeral 10 denotes a main body of an ultrasonic sterilizing apparatus; i.e., an apparatus main body, which includes a treatment vessel 11 and an operation section 13.

The treatment vessel 11 is composed of a container having a predetermined shape (in the present embodiment, flat-shaped container with its top open) and includes a bottom wall 12, and a side wall 15 raised from the periphery of the bottom wall 12. The interior of the treatment vessel 11 accommodates an unillustrated fluid (in the present embodiment, water) which is a medium for transmitting ultrasonic waves. A user may soak a diseased part of the body (e.g., feet) in the water, by placing that part (e.g., the feet) in the treatment vessel 11. Although, in the present embodiment the feet are put into the treatment vessel 11 of the ultrasonic sterilizing apparatus so that the diseased part of the feet are soaked in the water, alternatively, the user may soak a diseased part of the hands in the water by placing them in the treatment vessel 11. In this connection, a fluid other than water may be employed as the medium.

The bottom wall 12 has foot-placement sections p1 and p2, which are bilaterally-symmetrically formed in the shape of a pair of soles. A large number of projections 16 projecting upward are provided on the foot-placement sections p1 and p2. Also, first and second ultrasonic oscillation sections for generating ultrasonic waves are disposed at predetermined locations (three locations in the present embodiment) on the bottom wall 12. The first ultrasonic oscillation section includes a pair of pin-shaped ultrasonic vibrators 81 (first spreading devices), which are disposed on the foot-placement sections p1 and p2, respectively. The second ultrasonic oscillation section includes a single flat-shaped ultrasonic vibrator 82 (a second spreading device), which is disposed between the foot-placement sections p1 and p2.

As shown in FIG. 2, each of the ultrasonic vibrators 81 is provided projecting upward, so that when the feet are placed on the respective foot-placement sections p1 and p2, each transducer 81 is sandwiched by the big toe and the adjacent toe of the corresponding foot. Similarly, the ultrasonic vibrator 82 is provided projecting upward between the foot-placement sections p1 and p2, so as to be disposed between the arches of the respective feet. A plurality of upward-extending projections 17 are provided radially and at equal radial intervals around the ultrasonic vibrator 82. Although, in the present embodiment, each of the ultrasonic vibrators 81 is used for the toes of one's foot and is provided so as to be disposed between the big toe and the adjacent toe, it may be provided so as to be sandwiched by any adjacent toes of the foot. Alternatively, it may be used for the fingers of one's hand. Further, each of the ultrasonic vibrators 81 and 82 has such a height as to be soaked when the treatment vessel 11 is filled with a predetermined amount of water.

In the present embodiment, the large number of projections 16 and 17 provided on the bottom wall 12 not only provide a massage effect on the soles, but also enable a user to know where to place their feet by feel. As will be described hereinbelow, in the present embodiment, an unillustrated heater serving as a heating body is buried in a predetermined location in the bottom wall 12, and in this arrangement, the projections 16 and 17 prevent direct transmission of heat from the heater to the feet.

As shown in FIG. 3, the ultrasonic vibrator 81 includes a main body 83, an attachment portion 84, and a tubular portion 85, wherein the main body 83 includes a pin-shaped rod body; the attachment portion 84 is provided projecting radially outward at the bottom end of the main body 83; and the tubular portion 85 is provided projecting downward on the attachment portion 84. The ultrasonic vibrator 81 is attached to the bottom wall 12 by use of bolts bt1, with the tubular portion 85 being received in a depressed portion h1 formed at a predetermined location of the bottom wall 12.

An O-ring 86 serving as a seal member is held between the outer circumferential surface of the tubular portion 85 and the inner circumferential surface of the depressed portion h1, and a back surface of the attachment portion 84 is formed with an element-holding member am1 of a predetermined shape (in the present embodiment, a column-shaped space is formed). In the element-holding member am1, the top end and the side part are surrounded by the attachment portion 84, and the bottom end is open. An ultrasonic element 87, which is made from, for example, a ceramic transducer is attached on the top end of the element-holding member am1.

Notably, a through-hole h11, which is for the wiring to drive the ultrasonic element 87, is formed in the bottom part of the depressed portion h1.

The main body 83 has a predetermined diameter which allows the main body 83 to be disposed between toes of one's foot, and has a height which allows the top end of the main body 83 to project upward from between the toes when disposed therebetween. The top of the main body 83 is provided with a screw 90 serving as power adjustment, which is made from a material different from that of the main body 83 (in the present embodiment, stainless steel). This structure lessens the output of the ultrasonic waves radiated upward, and consequently amplifies the output of the ultrasonic waves radiated sideward (i.e., toward the toes of one's foot), to thereby effectively irradiate the toes with ultrasonic waves.

As shown in FIG. 4, the top end of the ultrasonic vibrator is closed by a planar wall body 88. The ultrasonic vibrator includes a main body 89 having a hollow cylindrical body, and a tubular portion (an attachment portion) 92 which projects downward from the main body 89. The ultrasonic vibrator 82 is attached to the bottom wall 12 by use of bolts bt2, with the tubular portion 92 being received in a depressed portion h2 formed at a predetermined location of the bottom wall 12.

The O-ring 86 serving as a seal member is held between the outer circumferential surface of the tubular portion 92 and the inner circumferential surface of the depressed portion h2, and the back surface of the wall body 88 is provided with an element-holding member am2 of a predetermined shape (in the present embodiment, a column-shaped space is formed). In the element-holding member am2, the top end is surrounded by the main body 89, the side part is surrounded by the tubular portion 92, and the bottom end is open. The top end of the element-holding member am2 is provided with the ultrasonic element 87, which is made of, for example, a ceramic transducer.

Notably, a through-hole h21 for the wiring to drive the ultrasonic element 87 is formed in the bottom part of the depressed portion h2. The ultrasonic vibrator 82 is larger in diameter than the ultrasonic vibrator 81, and has a predetermined height which allows the ultrasonic vibrator 82 to be disposed between the arches of the feet.

When the ultrasonic element 87 is driven, ultrasonic waves are generated not only on the front surface side thereof, but also on the back surface side thereof. If water is present on the back surface side of the ultrasonic element 87, the ultrasonic waves generated on the back surface side are transmitted across the water within the element-holding members am1 and am2 toward the bottom part of the depressed portions h1 and h2, to thereby reduce the irradiation energy of the ultrasonic waves generated on the front surface side. Moreover, the ultrasonic waves reflected from the bottom part of the depressed portions h1 and h2 are transmitted upward across the water within the element-holding members am1 and am2, to thereby generate interference between the ultrasonic waves generated on the front surface side and those generated on the back side of the ultrasonic element 87. As a result, hydroxyl radicals are not generated at the locations where the two types of ultrasonic waves interfere with each other.

As described above, in the present embodiment, the element-holding members am1 and am2 are formed on the back surface side of each ultrasonic element 87, and the element-holding members am1 and am2 are filled with air to thereby form an air layer therein.

Because the air layer prevents transmission of ultrasonic waves, only the ultrasonic waves generated on the front surface side of the ultrasonic element 87 may be transmitted through the water, to thereby amplify the irradiation energy thereof. The structure may also prevent interference between ultrasonic waves generated on the front surface side and those generated on the back surface side of the ultrasonic element 87, which enables generation of a sufficient amount of hydroxyl radicals.

Notably, the space which prohibits transmission of ultrasonic waves (i.e., a non-ultrasonic wave transmission space) is formed by the element-holding members am1 and am2. The non-ultrasonic wave transmission space is also formed by creation of a vacuum in the element-holding members am1 and am2.

In the present embodiment, the ultrasonic vibrators 81 and 82 are both made of a metal such as stainless steel, but they may also be made of such a material as glass or aluminum, that can transmit oscillation.

Next, the operation section 13 of the ultrasonic sterilizing apparatus of the above structure will be described.

The operation section 13 (FIG. 1) includes buttons bi (i=1, 2 . . . ), LED lamps ej (j=1, 2 . . . ), and a monitor m1, wherein the buttons bi are operation elements for performing various types of operations; the LED lamps ej are first display elements; and the monitor m1 is a second display element. An operator may perform various types of settings by pressing the buttons bi, and may confirm the settings and working conditions by the lighting of the LED lamps ej and display of the monitor m1.

A button b1, for example, is a power supply button, and the operator can turn on/off power by operating the button b1. When the power is turned on, an LED lamp e1 is lighted, to thereby display a state of power-on. A button b2 is a timer-setting button, and the operator can set a timer by operating the button b2. In this case, repeatedly pressing the button b2 can alter the setting of irradiation time with ultrasonic waves, and may display the remaining time on the monitor m1. A button b3 is a frequency-switching button, and the operator can switch a frequency of ultrasonic waves generated by the ultrasonic element 87 by operating the button b3. When the frequency is switched, a plurality of LED elements which structure an LED lamp e2 are selectively lighted.

A button b4 is an output-point-selecting button, and the operator can selectively drive only a predetermined ultrasonic vibrator among the ultrasonic vibrators 81 and 82 by operating the button b4. When a predetermined transducer is selected in accordance with a location of a diseased part, a plurality of LED elements which structure an LED lamp e3 are selectively lighted, and a plurality of LED elements which structure an LED lamp e4 for monitoring foot placement are also selectively lighted.

A button b5 is a temperature-selection button, and the operator can set the temperature of water accommodated in the treatment vessel 11 by operating the button b5. In this case, repeatedly pressing the button b5 can alter the setting of the temperature, and a plurality of LED elements which structure an LED lamp e5 are selectively lighted. The temperature of water accommodated in the treatment vessel 11 is controlled to fall within a range of 0° C. to 50° C. For controlling the temperature, for example, a heater serving as a heating body is buried at a predetermined location in the bottom wall 12, and a temperature sensor serving as a temperature detection section for detecting the temperature of water is disposed in the treatment vessel 11.

A button b6 is an ultrasonic output-selecting button, and the operator can switch the output of ultrasonic waves by operating the button b6. When a predetermined output is selected, a plurality of LED elements which structure an LED lamp e6 are selectively lighted, and a predetermined LED element among the plurality of LED elements in an output-indicator structured by an LED lamp e7 is lighted in a predetermined pattern.

A button b7 is a mode-selection button, and the operator can select an automatic mode or a manual mode by operating the button b7, wherein the automatic mode can automatically set the frequency, output, and irradiation time of ultrasonic waves, the water temperature, an irradiation location, etc.; and the manual mode can manually set the frequency, output, and irradiation time of ultrasonic waves, the water temperature, an irradiation location, etc. When a predetermined mode is selected, a plurality of LED elements which structure an LED lamp e8 are selectively lighted. A button b8 is an output-pattern-selecting button, and the operator can switch the output of ultrasonic waves, for example, once every second or once every five seconds by operating the button b8. When a predetermined output pattern is selected, a plurality of LED elements which structure an LED lamp e9 are selectively lighted.

Moreover, an LED lamp e10 is lighted when a water level in the treatment vessel 11 becomes lower than a predetermined threshold level.

Next, the control device of the ultrasonic sterilizing apparatus having the above structure will be described.

Figure 5:
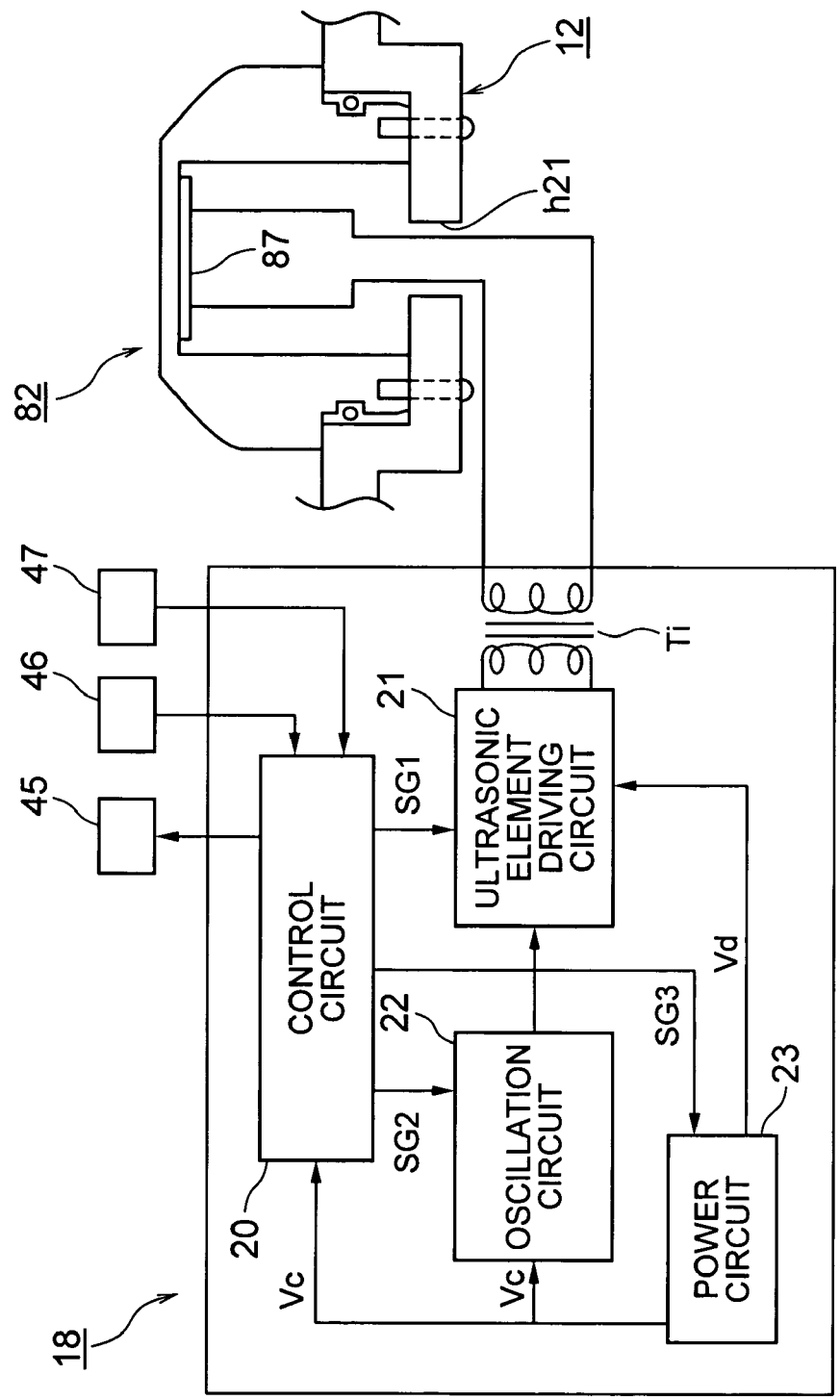
FIG. 5 Block diagram of a control device of the ultrasonic sterilizing apparatus according to the embodiment of the present invention.

FIG. 5 is a block diagram of a control device of the ultrasonic sterilizing apparatus according to the embodiment of the present invention.

In FIG. 5, reference numeral 18 denotes a driving section for driving the corresponding ultrasonic element 87; and reference numeral 20 denotes a control circuit serving as a control section. The control circuit 20 includes an unillustrated CPU, RAM, and ROM, wherein the CPU serves as a calculation unit; the RAM is used as a working memory when the CPU performs various types of calculation processes; and the ROM stores control programs, various types of data, etc. The CPU functions as a computer based on various types of programs, data, etc. The above-mentioned RAM, ROM, etc. constitute a recording unit. Also, an MPU and the like may be used instead of the CPU. The control circuit 20 performs feedback control in an automatic mode or in a manual mode, so as to set values for the frequency, output, and irradiation time of ultrasonic waves; the water temperature; an irradiation location; and the like.

Reference numeral 21 denotes an ultrasonic element driving circuit serving as driving processing means for driving the corresponding ultrasonic element 87. The ultrasonic element driving circuit 21 is connected with the corresponding ultrasonic element 87 via a trans Ti (i=1, 2, or 3); the circuit performs a driving process when it receives a control signal SG1 from the control circuit 20, and drives the corresponding ultrasonic element 87 at a predetermined frequency. Although only a single trans Ti is shown in FIG. 5, the trans T is are provided in a number equal to that of the ultrasonic elements 87, three trans T is in the present embodiment, each of which corresponds with one of the ultrasonic elements 87 included in a corresponding one of the three ultrasonic vibrators (i.e., the pair of ultrasonic vibrators 81 and the ultrasonic vibrator 82). Each trans Ti is provided for adjusting impedance, and for insulating between the corresponding ultrasonic element 87 and an element such as the ultrasonic element driving circuit 21 included in the driving section 18.

Reference numeral 22 denotes an oscillation circuit which receives a control signal SG2 from the control circuit 20, and oscillates at a controlled frequency falling within a range of 950 kHz to 2 MHz. Reference numeral 23 denotes a power circuit which applies a voltage of 5 V for control (Vc) to the control circuit 20 and the oscillation circuit 22, and receives a digital control signal SG3 from the control circuit 20 to thereby apply to the ultrasonic element driving circuit 21 a controlled voltage for driving (Vd) falling within a range of more than 0 V to 60 V.

In the present embodiment, the oscillation circuit 22 performs basic oscillation of 1.65 MHz. The ultrasonic element driving circuit 21 comprises a separately-excited oscillation circuit, receives and amplifies a signal of the basic oscillation, and drives the ultrasonic vibrators 81 and 82. Therefore, this structure may prevent changes in the frequency and output caused by external factors including the amount of water, and the state when one's feet are placed on the foot-placement sections p1 and p2. By virtue of including a circuit for compensating the frequency and a circuit for compensating a waveform, the ultrasonic element driving circuit 21 may apply a stable voltage to the ultrasonic elements 87. As a result, in each ultrasonic element 87, ultrasonic waves of the frequency falling within a range of 950 kHz to 2 MHz are generated with a controlled output falling within a range of 10 mW/cm$^2$ to 28 W/cm$^2$.

The temperature of water accommodated in the treatment vessel 11 is controlled to fall within a range of 0° C. to 50° C. For temperature control, for example, a heater 45 and if necessary, an unillustrated cooling device serving as a cooling body are buried at a predetermined location in the bottom wall 12, and a temperature sensor 46 is provided within the treatment vessel 11. The control circuit 20 is provided with an unillustrated temperature-control circuit serving as temperature-control processing means for controlling the temperature within the treatment vessel 11. The temperature-control circuit performs a temperature-control process, and reads the temperature detected by the temperature sensor 46, and turns on/off, for example, the heater 45 and the cooling device.

For detecting the water level within the treatment vessel 11, a water-level detector 47 is provided, wherein the water-level detector 47 outputs the detected water level, and transmits the sensor output to the control circuit 20. Unillustrated alarm processing means of the control circuit 20 performs an alarm process, reads the sensor output from the water-level detector 47, detects the water level, illuminates the LED lamp e10 when the water level becomes lower than a threshold level, and notifies the operator of the state of the water level.

Meanwhile, ultrasonic waves generated by the ultrasonic elements 87 are transmitted to the ultrasonic vibrators 81 and 82, and are propagated through water by means of the ultrasonic vibrators 81 and 82. At this time, the water accommodated in the treatment vessel 11 is decomposed by ultrasonic waves to thereby generate hydroxyl radicals and hydrogen atoms. Ultrasonic waves are also transmitted to one's feet both indirectly via the water, and directly via each of the ultrasonic vibrators 81 and 82. Similarly, the water in the body is decomposed by ultrasonic waves to thereby generate hydroxyl radicals and hydrogen atoms. When a fluid other than water is employed as a medium, ultrasonic waves are transmitted to the fluid, followed by decomposition of water in the fluid by the ultrasonic waves, to thereby generate hydroxyl radicals and hydrogen atoms.

That is, unillustrated hydroxyl radical generating processing means is formed by the ultrasonic element driving circuit 21, the hydroxyl-radical-generating means performs a hydroxyl-radical generating process, and the ultrasonic elements 87 are driven to thereby generate the hydroxyl radicals.

As a result, bacteria (e.g., microbes such as *Trichophyton* causing athlete's foot) may be sufficiently oxidized, decomposed, and sterilized at a diseased part of the body soaked in the water to thereby treat the diseased part.

In the present embodiment, for favorable treatment of a diseased part of the body, the amount of generated hydroxyl radicals falls within a range of 0.1 µM to 60 µM, which is a value measured by an electron spin resonance (ESR) spin trapping method (apparatus) with 5,5-dimethyl-1-pyrroline-N-oxide (DMPO).

The driving time of the ultrasonic elements 87 is one second or more, and is a time that does not affect cells and tissues in the human body. The higher the output of ultrasonic waves, the shorter the driving time.

Next, the ultrasonic deflection device for deflecting ultrasonic waves to thereby transmit ultrasonic waves to a diseased part of the body will be described.

Figure 6:
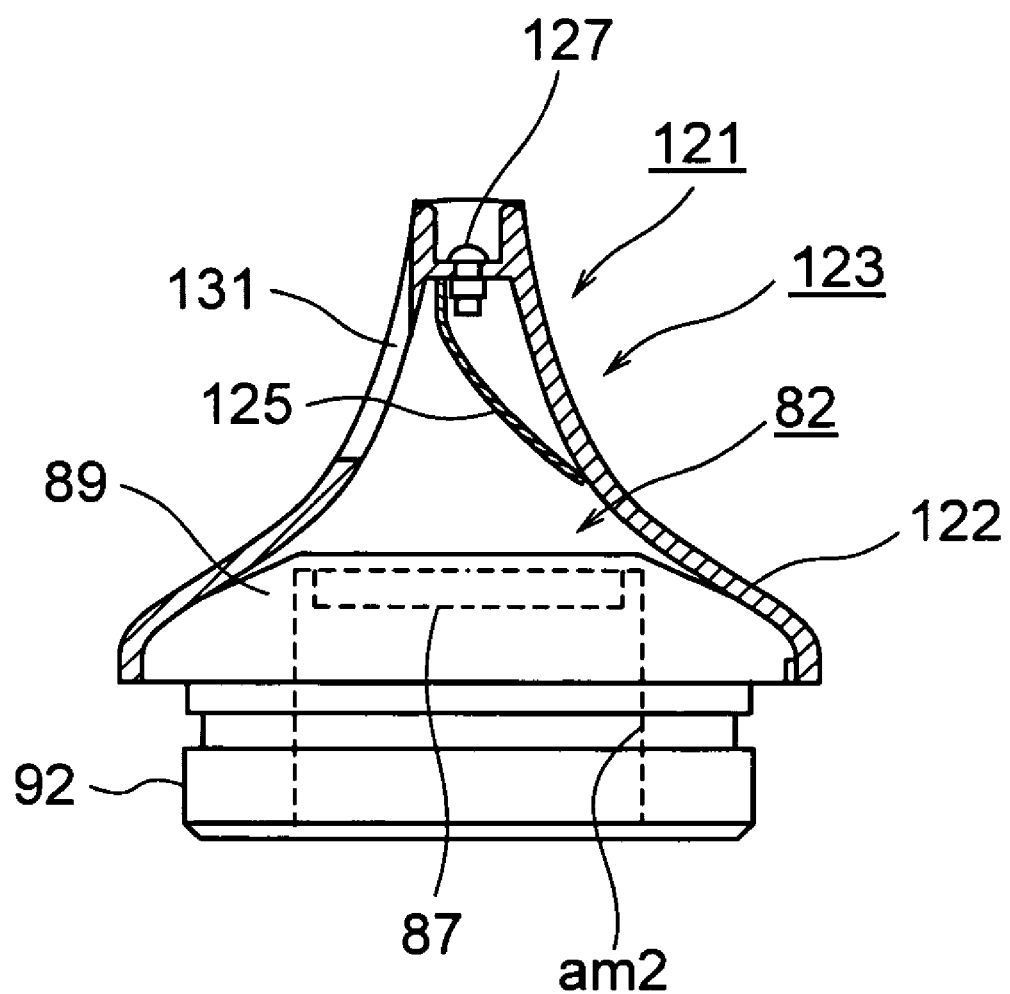
FIG. 6 View showing an ultrasonic deflection device attached to the flat-shaped ultrasonic vibrator in the ultrasonic sterilizing apparatus according to the embodiment of the present invention.

FIG. 6 is view showing ultrasonic deflection device attached to the flat-shaped ultrasonic vibrator in the ultrasonic sterilizing apparatus in the embodiment of the present invention.

In FIG. 6, reference numeral 82 denotes the ultrasonic vibrator; reference numeral 87 denotes the ultrasonic element included in the element-holding member am2; reference numeral 89 denotes the main body; reference numeral 92 denotes the tubular portion; and reference numeral 121 denotes an ultrasonic deflection device detachably disposed on the ultrasonic vibrator 82. The ultrasonic deflection device 121 includes a base 122 surrounding the main body 89; and a reflection-housing member 123 to stand upward from the base 122. The reflection-housing member 123 houses a reflecting plate 125 in a shape of a convex mirror having a curved reflecting surface which is attached to the top end of the reflection-housing member 123 by use of a bolt 127 serving as a fixed member. A window 131 is formed in the side part of the reflection-housing member 123.

After being generated by the ultrasonic element 87 and transmitted upward in water, ultrasonic waves are reflected by the reflecting plate 125, then deflected sideward and transmitted in water.

The ultrasonic deflection device 121 may be attached or detached to the ultrasonic vibrator 82 in accordance with the location of a diseased part of the body, to thereby effectively irradiate the diseased part with ultrasonic waves.

In the present embodiment, one's feet or other body parts may be placed in the treatment vessel 11 accommodating water, to thereby immerse the diseased part of such a body part. In such a case, if a plurality of people use the same treatment vessel 11 and treat their diseased parts, they may become infected with *Trichophyton* etc., even when the water accommodated in the treatment vessel 11 is changed to fresh one.

In order to solve the problem, a sheet-type container made from a flexible material (e.g., a plastic bag) may be set as an inner liner within the treatment vessel 11 and contain water, and the feet may be placed in the water contained therein. In this case, after completion of feet treatment, both the inner liner and the water contained therein are discarded to thereby lessen the possibility that a plurality of people are infected with *Trichophyton* or similar microorganisms.

In this case, when air enters between the inner lining and the ultrasonic vibrators 81 and 82, ultrasonic waves generated by each ultrasonic element 87 can not be transmitted to the water contained in the inner lining.

In order to solve the problem, a small amount of water is accommodated in the treatment vessel 11 and the inner lining is set thereon and the inner lining is filled with water, so as to prevent air from entering between the inner lining and the ultrasonic vibrators 81 and 82, to thereby reliably transmit ultrasonic waves generated by the ultrasonic elements 87 to the water contained in the inner lining.

The amount of water accommodated in the treatment vessel 11 is set so as to make the water level equal in height to the top ends of the ultrasonic vibrators 81 and 82. When the ultrasonic vibrators 81 and 82 each have a planar top surface, drops of water on the top surface of the ultrasonic vibrators 81 and 82 would suffice to enhance the adhesion between the inner lining and the ultrasonic vibrators 81 and 82.

EXAMPLE

A representative *Trichophyton* (in this case, *T. mentagrophytes*) was placed in a test tube, and was subjected to various sterilization conditions including frequency of ultrasonic waves, water temperature, voltage (Vd), and irradiation time. A method for evaluation was based on the count of *T. mentagrophytes*.

When the frequency was 1.65 MHz, and the amount of generated hydroxyl radicals was about 50 μM, the count of *T. mentagrophytes* showed no decrease at a water temperature of 30° C.

When the frequency was 1.65 MHz; voltage (Vd) was set so as to generate about 50 μM of hydroxyl radicals; and irradiation time was 5 minutes, the count of *T. mentagrophytes* decreased from one million to about 30 at a water temperature of 40° C. When the above-mentioned conditions were repeated, except that the irradiation time was changed to 10 minutes, the count of *T. mentagrophytes* decreased from one million to zero.

When the frequency was 1.65 MHz; voltage (Vd) was altered so as to generate about 1.25 μM or about 8 μM of hydroxyl radicals, respectively; and irradiation time was 10 minutes, the count of *T. mentagrophytes* decreased from one million to 5,000 at a water temperature of 40° C.

Moreover, when the frequency was 1.65 MHz; voltage (Vd) was altered so as to generate about 8 μM or about 50 μM of hydroxyl radicals, respectively; and irradiation time fell within a range of 5 minutes to 10 minutes, the count of *T. mentagrophytes* decreased from one million to zero at a water temperature of 50° C.

These results suggest that setting water temperature to 40° C. or more drastically improves a sterilization effect. Notably, since one's feet must be placed in the treatment vessel 11, the water temperature preferably falls within a range of 40° C. to 43° C.

Meanwhile, when the feet are irradiated with ultrasonic waves, the skin may be damaged. When cultured cells were directly irradiated with ultrasonic waves with voltage (Vd) set so as to generate about 24 μM of hydroxyl radicals for 10 minutes of irradiation time, cell count decreased by 50%. In contrast, when the amount of generated hydroxyl radicals was set to be about 4 μM, and the irradiation time was 10 minutes, cell count decreased by 10%.

Next, the result of an experiment in which athlete's foot was treated by irradiation with ultrasonic waves will be described.

In this experiment, the feet were irradiated with ultrasonic waves under the following conditions: the amount of generated hydroxyl radicals fell within a range of 0.1 μM to 2 μM, and water temperature fell within a range of 10° C. to 20° C. When irradiation time for every irradiation treatment was 20 minutes and the irradiation was repeated 3 to 10 times, a diseased part was completely cured. Thus, when the irradiation with ultrasonic waves is repeated, the amount of generated hydroxyl radicals in every irradiation treatment may fall within a range of 0.1 μM to 2 μM.

These results suggest that in the ultrasonic sterilizing apparatus which sterilizes *Trichophyton* or a similar microorganism, the following conditions are preferred: water temperature falls within a range of 5° C. to 50° C., the amount of hydroxyl radicals generated falls within a range of 0.1 μM to about 60 μM, and the irradiation time for every diseased part is 20 minutes or less for every irradiation treatment.

According to another preferred mode, the following conditions are employed: generation of hydroxyl radicals is increased to fall within a range of about 20 μM to about 50 μM; shorter irradiation time for every diseased part; and repeated irradiation treatments. In this case, when irradiation time is 2 minutes or less, *Trichophyton* or a similar microorganism may be sterilized without adverse effects on the human body.

When the frequency of ultrasonic waves was set to 1 MHz, the same result was obtained under the aforementioned sterilization conditions.

The present invention is not limited to the above-described embodiment. Numerous modifications and variations of the present invention are possible in light of the spirit of the present invention, and they are not excluded from the scope of the present invention.

The invention claimed is:

1. An ultrasonic treatment apparatus comprising:
   (a) a treatment vessel for accommodating a medium;
   (b) an ultrasonic element for generating ultrasonic waves in the treatment vessel, irradiating the medium accommodated in the treatment vessel with the ultrasonic waves, and decomposing water present in the medium to generate hydroxyl radicals;
   (c) an ultrasonic element driving circuit for driving the ultrasonic element;
   (d) an operation section for setting given sterilization conditions determined based on the amount of the generated hydroxyl radicals upon generation of the ultrasonic waves;
   (e) a spreading device provided on a bottom wall of the treatment vessel and comprising a main body projecting upward from the bottom wall and immersed in the medium accommodated in the treatment vessel, the spreading device spreading ultrasonic waves generated by the ultrasonic element in the treatment vessel; and
   (f) an ultrasonic deflection device detachably disposed on the top of the main body, and deflecting the ultrasonic waves generated by the ultrasonic element sidewards.

2. The ultrasonic treatment apparatus according to claim 1, further comprising hydroxyl radical generating processing means which generates hydroxyl radicals in an amount falling within a range of 0.1 μM to 60 μM.

3. The ultrasonic treatment apparatus according to claim 1, further comprising temperature control processing means which sets the temperature of the medium so as to fall within a range of 5° C. to 50° C.

4. The ultrasonic treatment apparatus according to claim 1, wherein the main body of the spreading device has a rod-shaped body projecting upward from the bottom wall and immersed in the medium accommodated in the treatment vessel.

5. The ultrasonic treatment apparatus according to claim 1, wherein the main body of the spreading device has a column body projecting upward from the bottom wall and immersed in the medium accommodated in the treatment vessel.

6. The ultrasonic treatment apparatus according to claim 1, wherein the spreading device has an air layer on a back surface side of the ultrasonic element.

7. The ultrasonic treatment apparatus according to claim 1, wherein the ultrasonic deflection device comprises a reflecting housing member, extending upward from the bottom wall and surrounding the spreading device, and a convex mirror mounted within the reflecting housing member, above the spreading device.

* * * * *